(12) United States Patent
Tan

(10) Patent No.: US 10,687,870 B2
(45) Date of Patent: Jun. 23, 2020

(54) INTRAMEDULLARY APPARATUS AND METHODS OF TREATING BONE FRACTURE USING THE SAME

(71) Applicant: Ta-Lun Tan, Taipei (TW)

(72) Inventor: Ta-Lun Tan, Taipei (TW)

( * ) Notice: Subject to any disclaimer, the term of this patent is extended or adjusted under 35 U.S.C. 154(b) by 122 days.

(21) Appl. No.: 15/958,173

(22) Filed: Apr. 20, 2018

(65) Prior Publication Data

US 2018/0235679 A1 Aug. 23, 2018

Related U.S. Application Data

(62) Division of application No. 14/257,292, filed on Apr. 21, 2014, now Pat. No. 9,949,771, which is a division of application No. 13/791,357, filed on Mar. 8, 2013, now Pat. No. 8,721,644.

(51) Int. Cl.
| | |
|---|---|
| *A61B 17/72* | (2006.01) |
| *A61B 17/17* | (2006.01) |
| *A61B 17/56* | (2006.01) |
| *A61B 90/00* | (2016.01) |

(52) U.S. Cl.
CPC ...... *A61B 17/7233* (2013.01); *A61B 17/1725* (2013.01); *A61B 90/39* (2016.02); *A61B 17/72* (2013.01); *A61B 2017/564* (2013.01)

(58) Field of Classification Search
CPC ......... A61B 17/88; A61B 17/68; A61B 17/72; A61B 17/7208–7241
See application file for complete search history.

(56) References Cited

U.S. PATENT DOCUMENTS

| | | | | |
|---|---|---|---|---|
| 2010/0130978 A1* | 5/2010 | Orbay | ............... | A61B 17/1782 606/62 |
| 2010/0217337 A1* | 8/2010 | Groh | .................. | A61B 17/1725 606/86 R |
| 2011/0218531 A1* | 9/2011 | Orbay | .................... | A61B 17/56 606/62 |
| 2014/0364859 A1* | 12/2014 | Wieland | ................. | A61B 17/72 606/97 |
| 2015/0073414 A1* | 3/2015 | Rogachefsky | ..... | A61B 17/7291 606/64 |
| 2015/0157467 A1* | 6/2015 | McGinley | .............. | A61B 17/15 606/86 R |
| 2015/0265361 A1* | 9/2015 | Blau | .................. | A61B 17/1703 606/67 |

* cited by examiner

*Primary Examiner* — Tessa M Matthews
(74) *Attorney, Agent, or Firm* — Osha Liang LLP

(57) ABSTRACT

In one aspect of the disclosure, an intramedullary (IM) apparatus for treating a fractured bone of an animal includes an IM nail elongated along a longitudinal axis and having at least three locking holes equally distantly defined thereon along the longitudinal axis, and a positional reference member having a longitudinal vernier scale thereon. The IM nail is configured to be inserted to a medullary cavity of a bone fragment, such that the IM nail is fixable to the bone fragment by a locking member correspondingly inserted into one of the locking holes through the bone fragment. The positional reference member is configured to be detachably mounted to the IM nail by two positioning members inserted into two of the locking holes such that the longitudinal vernier scale is parallel to the longitudinal axis of the IM nail, and each of the locking holes is locatable by the longitudinal vernier scale.

6 Claims, 22 Drawing Sheets

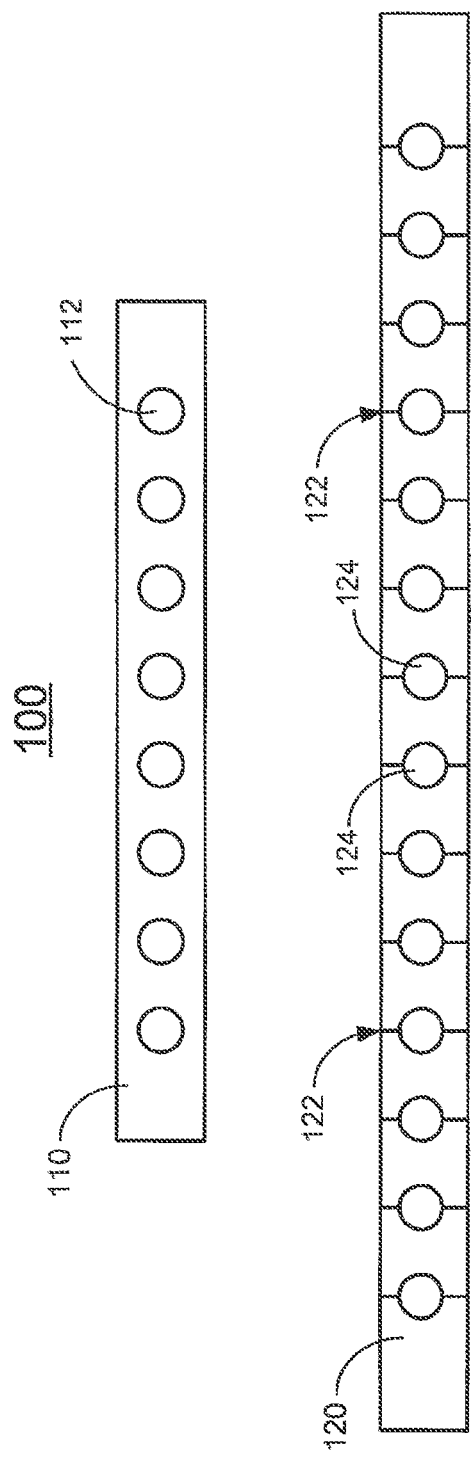

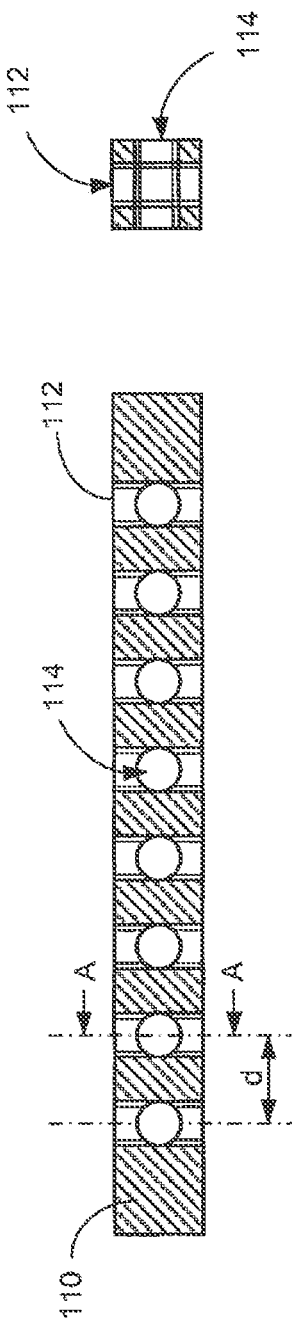

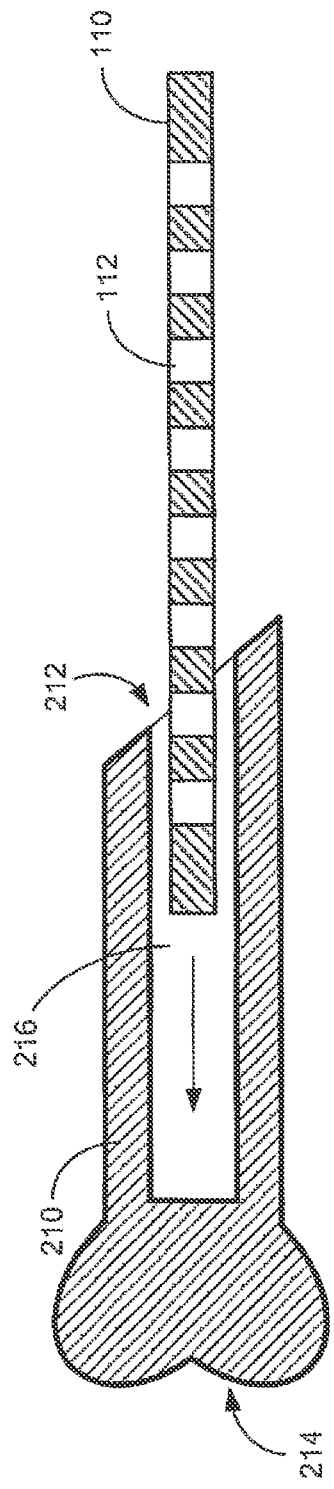
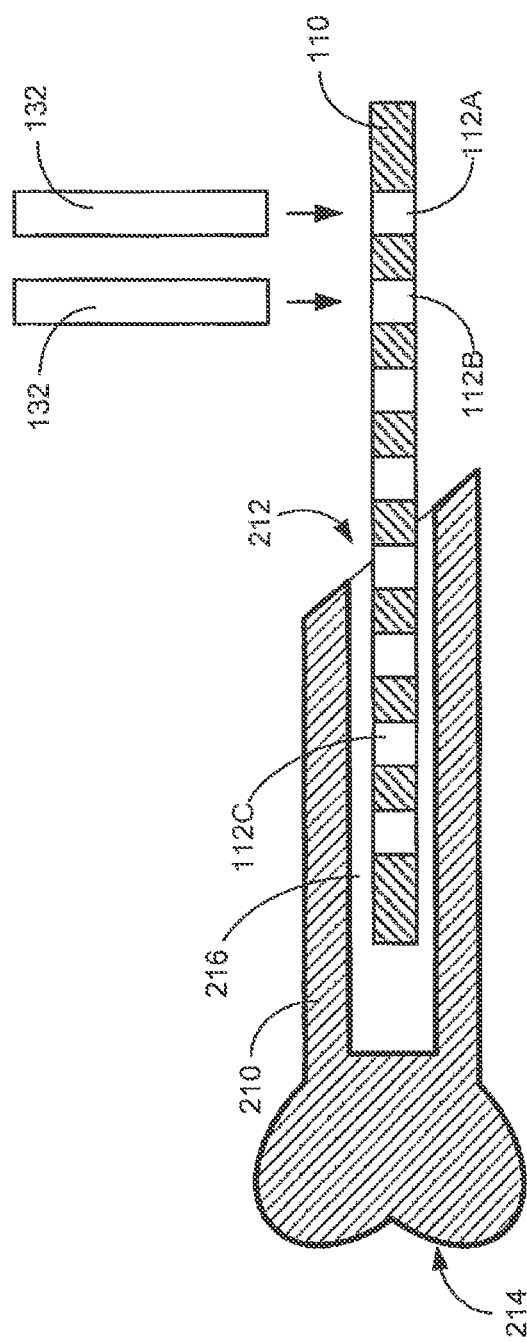
FIG. 3A
FIG. 3B

INTRAMEDULLARY APPARATUS AND METHODS OF TREATING BONE FRACTURE USING THE SAME

CROSS-REFERENCE TO RELATED APPLICATIONS

This Application is a divisional application and claims benefit under 35 U.S.C. § 120 to U.S. patent application Ser. No. 14/257,292, filed Apr. 21, 2014, which claims benefit to U.S. patent application Ser. No. 13/791,357, filed Mar. 8, 2008, issued as U.S. Pat. No. 8,721,644, on May 13, 2014. U.S. patent application Ser. No. 14/257,292 and patent application Ser. No. 13/791,357 are incorporated by reference in their entirety herein.

FIELD OF THE INVENTION

The present disclosure generally relates to bone fracture treatments, and more particularly to an intramedullary (IM) apparatus and methods of treating bone fracture using the same.

BACKGROUND OF THE INVENTION

An intramedullary (IM) nail, also known as an IM rod or inter-locking nail, is a long rigid rod used to treat fractures of bones of the body. When bone fracture occurs, an IM nail may be inserted (in some occasions forced) into the medullary cavity of the fractured bone to fix and maintain relative positional stability of the fractured bone parts. IM nails are particularly useful in treating fractures of long bones of the body.

A long bone has two joint ends connected to the joints. In a typical simple bone fracture case where a long bone is fractured into two bone fragments, each bone fragment would have a fractured end corresponding to each other, and at least one of the bone fragment is deviated from its original position due to the fracture in most cases. Thus, an IM nail may be inserted into the medullary cavity of the fractured long bone to fix the two bone fragments. Specifically, to place the IM nail into the medullary cavity of the fractured bone, the IM nail is inserted to the medullary cavity of one bone fragment from the fractured end. Then, the bone fragment can be forced back to its original position corresponding to the other bone fragment, and the IM nail can be pushed toward the medullary cavity of the other bone fragment such that the IM nail is located to be disposed between the fractured ends of the two bone fragments. Thus, the bone fragments can be fixed to the IM nail by a plurality of locking members, such as screws or pins. In a typical comminuted bone fracture case where a long bone is fractured into many (generally three or more) bone fragments, the IM nail may be fixed to the two bone fragments at the end of the comminuted long bone, and then the other bone fragments between these two bone fragments at the end may be disposed and fixed on the IM nail.

Generally, the IM nail may have a plurality of locking holes, such as screw holes and pin holes, such that the locking member (for example, a screw or a pin) may be used to lock the bone fragment to the IM nail. Fixing of the bone fragment to the IM nail may be done by drilling a hole on the bone fragment corresponding to the position of one of the locking holes of the IM nail such that the locking member may be inserted to the locking hole through the hole on the bone fragment. However, the fixing is generally difficult because the locking holes of the IM nail are hidden in the medullary cavity of the bone fragment and are difficult to locate.

Further, the length of the IM nail must be longer than the length of the bone fragment such that there will be an exposed part of the IM nail for the doctor to hold and locate the position of the IM nail within the medullary cavity of the bone fragment. Thus, to enable the bone fragment to be forced back to its original position, the IM nail must be forced to pass through the joint end of the bone fragment such that, when the bone fragment to be forced back to its original position corresponding to the other bone fragment, the doctor may push the exposed IM nail part from the joint end toward the medullary cavity of the other bone fragment. In this way, the pass-through of the IM nail may be destructive to the joint.

Therefore, a heretofore unaddressed need exists in the art to address the aforementioned deficiencies and inadequacies.

SUMMARY OF THE INVENTION

The present disclosure, in one aspect, relates to an intramedullary (IM) apparatus for treating a fractured bone of an animal. The IM apparatus includes an IM nail elongated along a longitudinal axis and having at least three locking holes equally distantly defined thereon along the longitudinal axis, and a positional reference member having a longitudinal vernier scale thereon. The IM nail is configured to be inserted to a medullary cavity of a bone fragment of the fractured bone, such that the IM nail is fixable to the bone fragment by a locking member correspondingly inserted into one of the locking holes through the bone fragment. The positional reference member is configured to be detachably mounted to the IM nail by two positioning members inserted into two of the locking holes such that the longitudinal vernier scale is parallel to the longitudinal axis of the IM nail, and each of the locking holes is locatable by the longitudinal vernier scale.

In one embodiment, the IM apparatus further includes a plate configured to be positioned outside the bone fragment and detachably fixed to the bone fragment and the IM nail by the locking member.

In one embodiment, the locking holes are through-holes substantially perpendicular to the longitudinal axis. In a further embodiment, the locking holes include at least one vertical locking hole perpendicular to the longitudinal axis in a vertical direction, and at least one horizontal locking hole perpendicular to the longitudinal axis in a horizontal direction in one embodiment, the positional reference member has a plurality of mounting holes corresponding to the two positioning members.

In one embodiment, the locking member and the positioning members are screws, and the locking holes are screw holes corresponding to the screws.

In one embodiment, the IM nail is made of a metal or dissolvable artificial skeletal material.

Another aspect of the present disclosure relates to a method of fixing an intramedullary (IM) apparatus to a bone fragment of a fractured bone of an animal, the method comprising: inserting an IM nail into a medullary cavity of the bone fragment, wherein the IM nail is elongated along a longitudinal axis and has at least three locking holes equally distantly defined thereon along the longitudinal axis, such that at least one of the locking holes is hidden by the bone fragment and at least two of the locking holes are exposed from the bone fragment; mounting a positional reference member to the IM nail by two positioning members inserted into the at least two exposed locking holes, such that a longitudinal vernier scale on the positional reference member is parallel to the longitudinal axis of the IM nail; locating the at least one hidden locking hole in the bone fragment by the longitudinal vernier scale of the positional reference member, and fixing the IM nail to the bone fragment by inserting a locking member to the located hidden locking hole through the bone fragment.

In one embodiment, the method further includes: drilling a hole on the bone fragment corresponding to the located hidden locking hole such that the IM nail is fixable to the bone fragment by inserting the locking member through the hole to the located hidden locking hole.

In one embodiment, the locking member and the positioning members are screws, and the locking holes are screw holes corresponding to the screws.

In one embodiment, the IM nail is made of a metal or dissolvable artificial skeletal material.

In another aspect, a method of treating a fractured bone of an animal using an intramedullary (IM) apparatus includes: inserting an IM nail into a medullary cavity of a first bone fragment of the fractured bone from a fracture end of the first bone fragment, wherein the IM nail is elongated along a longitudinal axis and has a plurality of locking holes positioned along the longitudinal axis, such that the locking holes are hidden in the first bone fragment, and an exposed part of the IM nail from the fracture end of the first bone fragment has at least two of the locking holes; cutting a slot along the longitudinal axis on the first bone fragment, such that at least two of the hidden locking holes in the first bone fragment is exposed through the slot; mounting a positional reference member to the IM nail by two positioning members inserted into the at least two exposed locking holes through the slot, such that a longitudinal vernier scale on the positional reference member is parallel to the longitudinal axis of the IM nail; inserting the exposed part of the IM nail into a medullary cavity of a second bone fragment of the fractured bone from a fracture end of the second bone fragment such that the at least one locking hole on the exposed part of the IM nail is hidden in the second bone fragment; locating the at least one hidden locking hole in the second bone fragment by the longitudinal vernier scale of the positional reference member; and fixing the IM nail to the second bone fragment by inserting a locking member to the located hidden locking hole through the second bone fragment.

In one embodiment, the method further includes: removing the positional reference member, and fixing the IM nail to the first bone fragment by the positioning members to the at least two exposed locking holes through the slot.

In one embodiment, the method further includes: moving the IM nail in the first bone fragment towards the second bone fragment by pushing the positioning members along the slot towards the fractured end of the first bone fragment.

In one embodiment, the method further includes: drilling a hole on the second bone fragment corresponding to the located hidden locking hole such that the IM nail is fixable to the second bone fragment by inserting the locking member through the hole to the located hidden locking hole.

In one embodiment, the locking member and the positioning members are screws, and the locking holes are screw holes corresponding to the screws.

In one embodiment, the IM nail is made of a metal or dissolvable artificial skeletal material.

Another aspect of the present disclosure relates to a method of treating a comminuted fractured bone of an animal using an intramedullary (IM) apparatus. The method includes: inserting an IM nail into a medullary cavity of a first bone fragment of the fractured bone from a fracture end of the first bone fragment, wherein the IM nail is elongated along a longitudinal axis and has at least four of locking holes positioned along the longitudinal axis, such that at least one of the locking holes is hidden in the first bone fragment, and an exposed part of the IM nail from the fracture end of the first bone fragment has at least three of the locking holes; inserting the exposed part of the IM nail into a medullary cavity of a second bone fragment of the fractured bone from a fracture end of the second bone fragment such that the at least one of the locking holes on the exposed part of the IM nail is hidden in the second bone fragment, and at least two of the locking holes are exposed; mounting a positional reference member to the IM nail by two positioning members inserted into the at least two exposed locking holes, such that a longitudinal vernier scale on the positional reference member is parallel to the longitudinal axis of the IM nail; locating the at least one hidden locking hole in the first bone fragment and the at least one hidden locking hole in the second bone fragment by the longitudinal vernier scale of the positional reference member, fixing the IM nail to the first and second bone fragments by inserting two locking members to the located hidden locking holes through the first and second bone fragments, respectively; and fixing a plurality of third bone fragments of the fractured bone on the IM nail, wherein the third bone fragments are positioned between the first and second bone fragments.

In one embodiment, fixing the third bone fragments further includes: removing the positional reference member and the two positioning members; disposing the third bone fragments of the fractured bone on the IM nail, wherein each of the third bone fragments correspond to the at least one of the at least two exposed locking holes; and fixing each of the third bone fragments to the IM nail by inserting the locking members to the at least two exposed locking holes through the third bone fragments, respectively.

In one embodiment, the locking member and the positioning members are screws, and the locking holes are screw holes corresponding to the screws.

In one embodiment, the IM nail is made of a metal or dissolvable artificial skeletal material.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment, and wherein:

FIG. 1B shows schematically a top view of the IM apparatus according to one embodiment of the present disclosure;

FIG. 1C shows schematically a cross-sectional view of an IM nail of the IM apparatus according to another embodiment of the present disclosure;

FIGS. 3A-3F show fixing an IM apparatus to a bone fragment according to one embodiment of the present disclosure;

DETAILED DESCRIPTION OF THE INVENTION

Figure 1A:
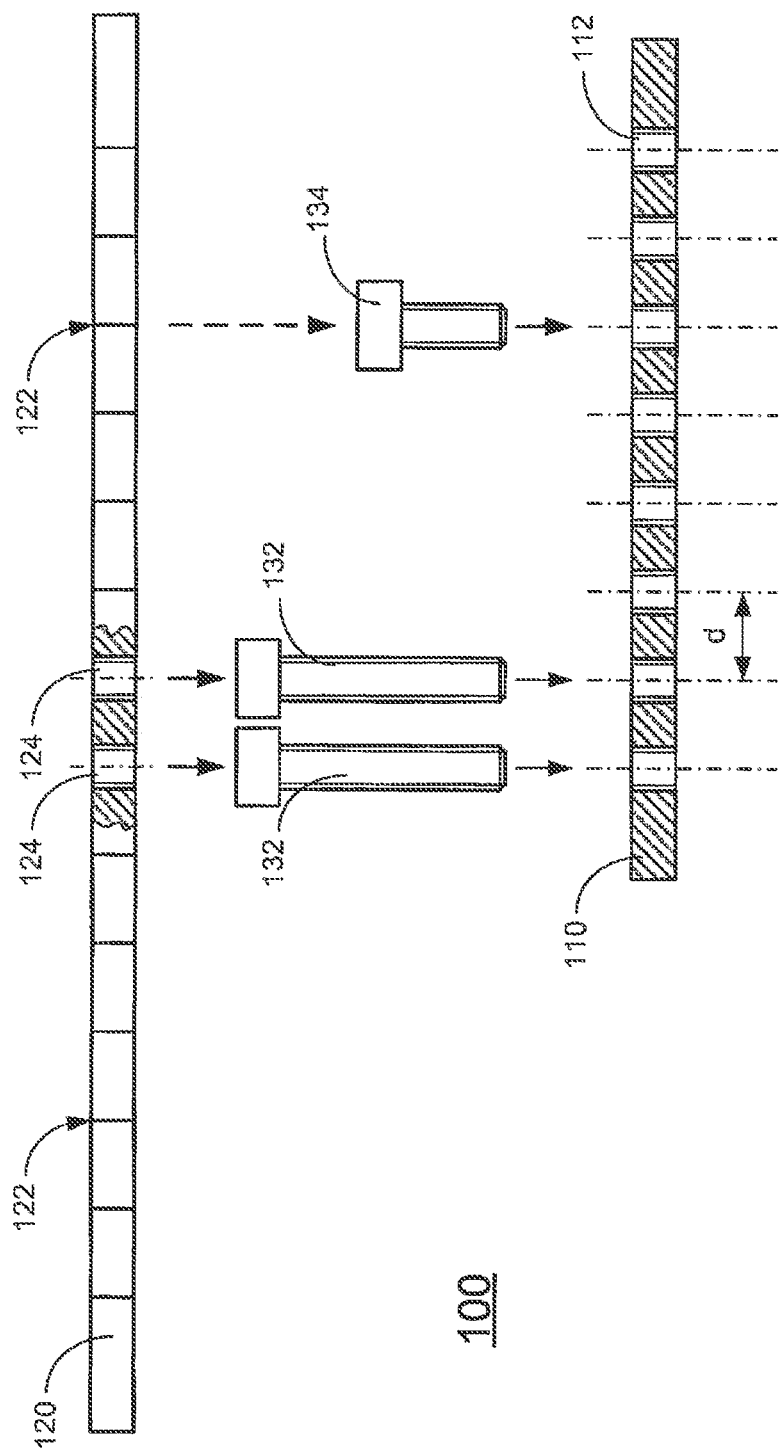
FIG. 1A shows schematically a plain view of an IM apparatus according to one embodiment of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising" or "includes" and/or "including" or "has" and/or "having" when used herein, specify the presence of stated features, regions, integers, steps, operations, elements, parts, segments and/or components, but do not preclude the presence or addition of one or more other features, regions, integers, steps, operations, elements, segments, components, and/or groups thereof.

It will be understood that, although the terms first, second, third etc. may be used herein to describe various elements, components, regions, layers and/or sections, these elements, components, regions, layers, segments and/or sections should not be limited by these terms. These terms are only used to distinguish one element, component, region, layer, segment or section from another element, component, region, layer, segment or section. Thus, a first element, component, region, layer, segment or section discussed below could be termed a second element, component, region, layer, segment or section without departing from the teachings of the present disclosure.

Furthermore, relative terms, such as "lower" or "bottom" and "upper" or "top", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper", depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The description will be made as to the embodiments of the present disclosure in conjunction with the accompanying drawings in FIGS. 1-5E. In accordance with the purposes of this disclosure, as embodied and broadly described herein, this disclosure, in one aspect, relates to an IM apparatus and methods of treating bone fractures using the same.

FIGS. 1A and 1B show schematically an IM apparatus according to one embodiment of the present disclosure, where FIG. 1A shows a plain view and FIG. 1B shows a top view. The IM apparatus 100 includes an IM nail 110 and a positional reference member 120, which may be used for treating a fractured bone of an animal. Further, a plurality of positioning members 132 and locking members 134 are provided for positioning and locking of the IM nail 110. In certain embodiments, the locking members 134 and the positioning members 132 are screws, pins or other fixing or locking structure or device.

The IM nail 110 is elongated along a longitudinal axis, i.e. the horizontal direction as shown in FIGS. 1A and 1B, and has a plurality of locking holes 112 equally distantly defined thereon along the longitudinal axis. As shown in FIGS. 1A and 1B, the IM nail 110 has eight locking holes 112. In certain embodiments, the IM nail 110 may have at least three locking holes 112. The locking holes 112 may be throughholes substantially perpendicular to the longitudinal axis of the IM nail 110 corresponding to the positioning members 132 and the locking members 134, and when the positioning members 132 and the locking members 134 are screws, the locking holes 112 may be screw holes corresponding to the screws. The IM nail 110 is configured to be inserted to a medullary cavity of a bone fragment of the fractured bone, such that the IM nail 110 is fixable to the bone fragment by the locking member 134 correspondingly inserted into one of the locking holes 112 through the bone fragment. In certain embodiments, the IM nail 110 is made of a metal or dissolvable artificial skeletal material.

The positional reference member 120 has a longitudinal vernier scale 122 thereon for locating the locking holes 112 on the IM nail 110. Specifically, the positional reference member 120 is configured to be detachably mounted to the IM nail 110 by two positioning members 132 inserted into two of the locking holes 112. Thus, the longitudinal vernier scale 122 would be parallel to the longitudinal axis of the IM nail 110, and each of the locking holes 112 would be locatable by the longitudinal vernier scale. In certain embodiments, the positional reference member 120 has a plurality of mounting holes 124 corresponding to the two positioning members 132, and the positions of the mounting holes 124 correspond to the longitudinal vernier scale 122 such that the longitudinal vernier scale 122 may directly locate the position of the locking holes 112 on the IM nail 110.

The size and shape of the IM nail 110 may differ according to the use of the IM nail 110. Factors used in determining the size and shape of the IM nail 110 include the size of the animal being treated, the size and bone structure of the fractured bone, and other medical factors to be considered. For example, the IM nail 110 may include a three-dimensional structure as shown in the cross-sectional view of FIG. 1C, with the locking holes 112 and 114 existing in two different directions (vertical and horizontal) of the IM nail 110, such that the locking member 134 may be inserted in any of the directions of the IM nail 110. In certain embodiments, the locking holes 112 and 114 may be individually or concurrently provided. In certain embodiments, the IM nail 110 may include at least one vertical locking hole 112 perpendicular to the longitudinal axis in a vertical direction, and at least one horizontal locking hole 114 perpendicular to the longitudinal axis in a horizontal direction.

Figure 2A:
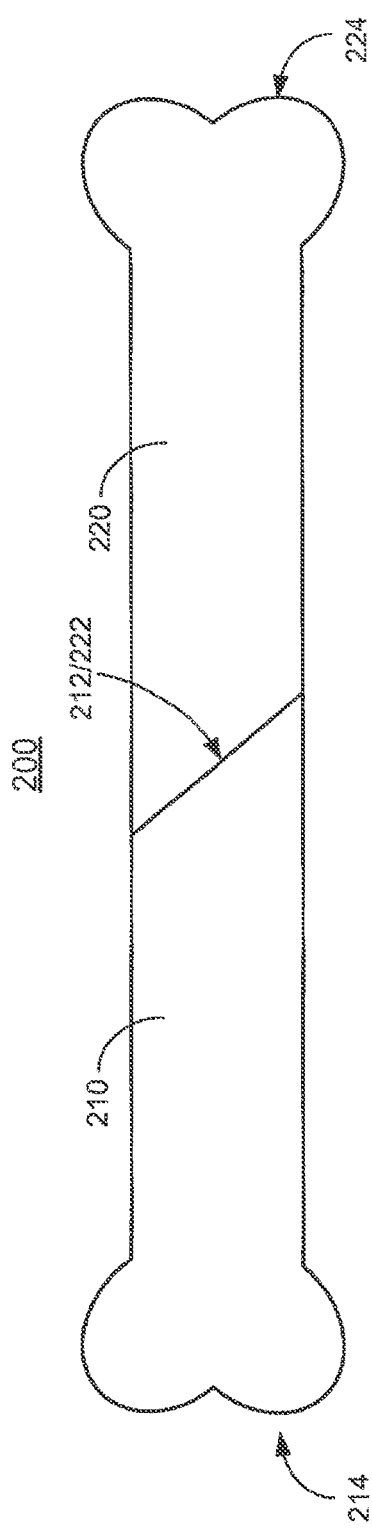
FIG. 2A shows schematically a fractured bone according to one embodiment of the present disclosure.
Figure 2B:
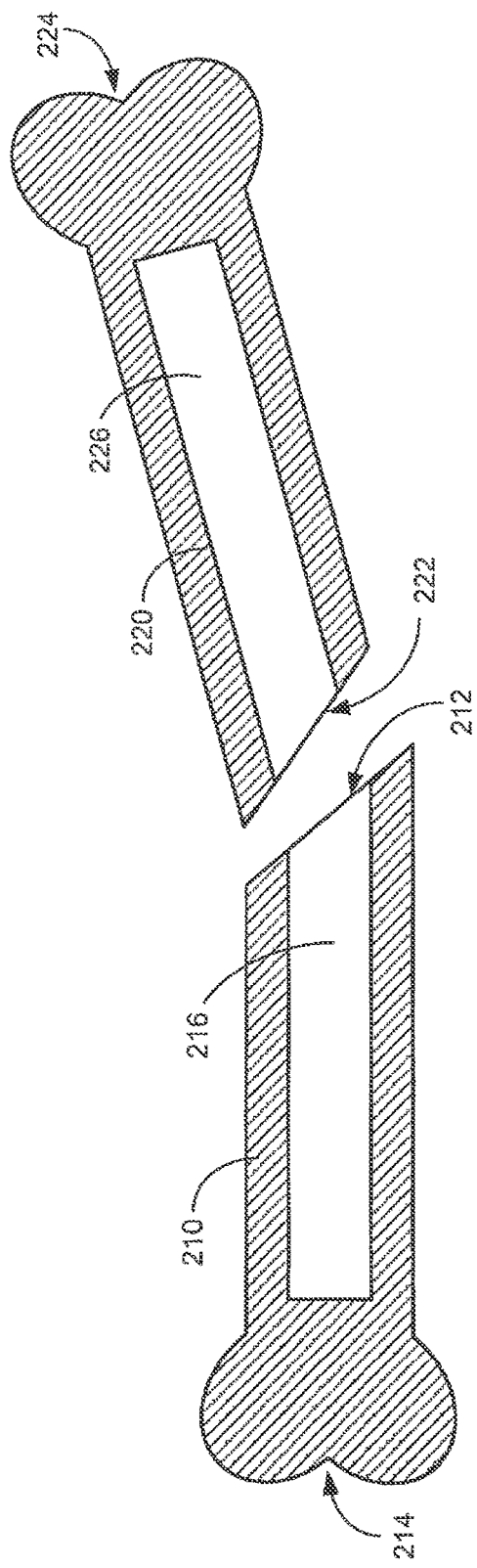
FIG. 2B shows schematically a cross-sectional view of the fractured bone according to one embodiment of the present disclosure.

FIGS. 2A and 2B show schematically a fractured bone according to one embodiment of the present disclosure. In this embodiment, the fractured bone 200 is fractured into two bone fragments, including a first bone fragment 210 and a second bone fragment 220. The first bone fragment 210 has a fractured end 212 and a joint end 214, and has a medullary cavity 216. Similarly, the second bone fragment 220 has a fractured end 222 and a joint end 224, and has a medullary cavity 226. As shown in FIG. 2A, the fractured ends 212 and 222 of the two bone fragments 210 and 220 correspond to each other in the original position of the fractured bone 200. Generally, one of the bone fragments 210 and 220 may be deformed or deviated from its original position, as shown in FIG. 2B.

Figure 2C:
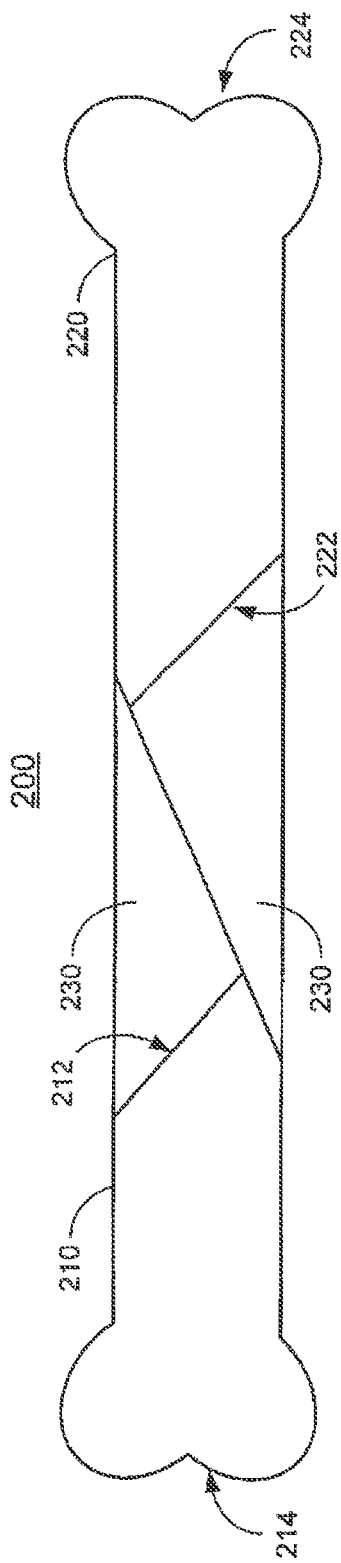
FIG. 2C shows schematically a comminuted fractured bone according to one embodiment of the present disclosure.
Figure 2D:
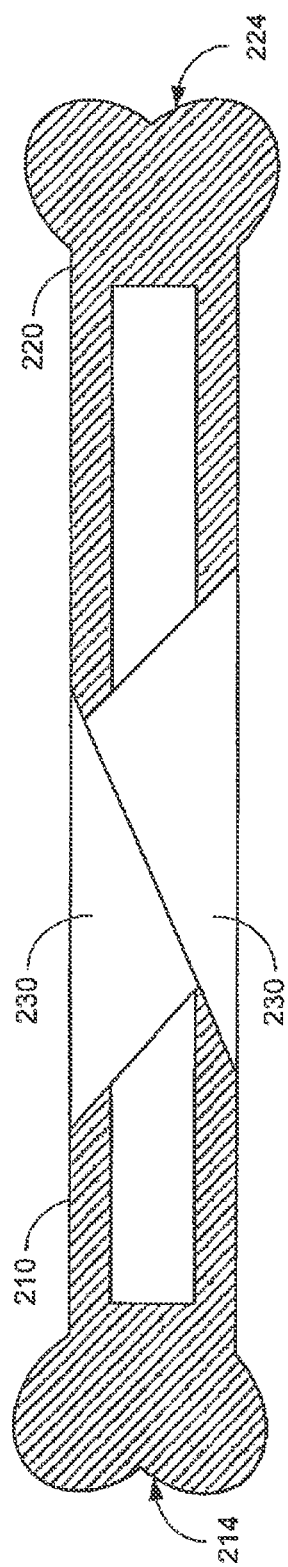
FIG. 2D shows schematically a cross-sectional view of the comminuted fractured bone according to one embodiment of the present disclosure.

FIGS. 2C and 2D show schematically a comminuted fractured bone according to one embodiment of the present disclosure. In this embodiment, the fractured bone 200 is fractured into four bone fragments, including a first bone fragment 210 and a second bone fragment 220 at the two ends of the fractured bone 200, and two third bone fragments 230 between the first and second bone fragments 210 and 220. The first bone fragment 210 has a fractured end 212 and a joint end 214. Similarly, the second bone fragment 220 has a fractured end 222 and a joint end 224. The third bone fragments 230 are comminuted bone pieces which does not connected to the joints.

Figure 3C:
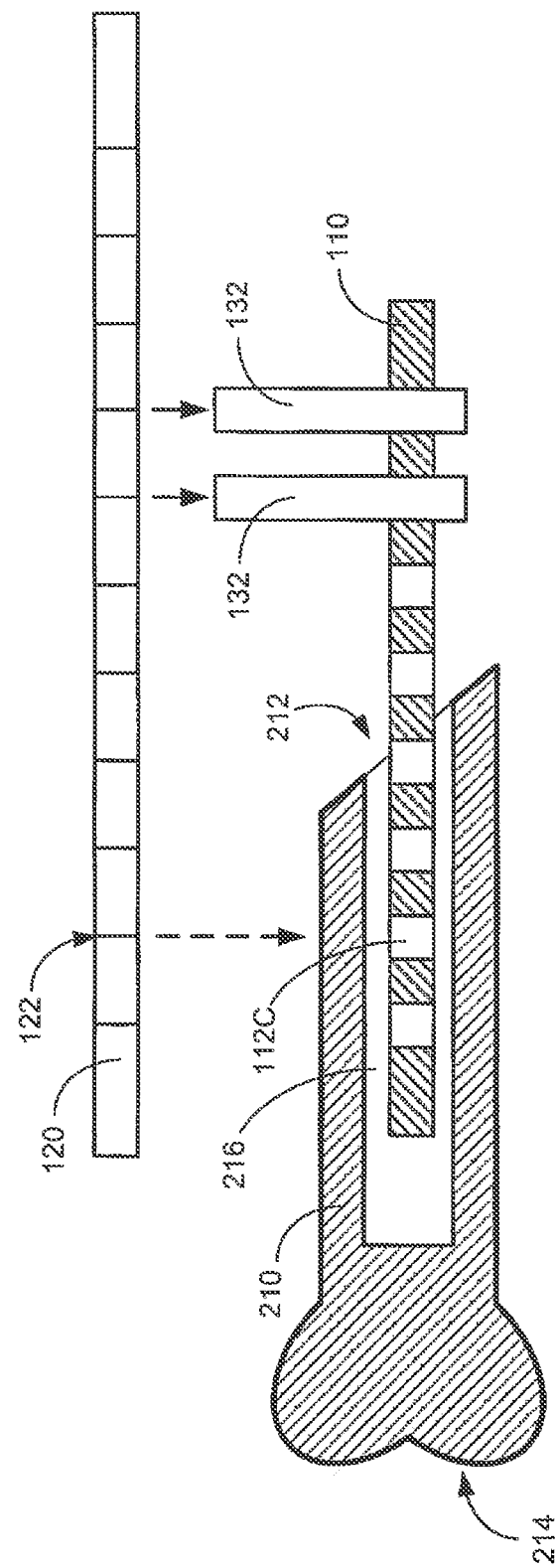

FIGS. 3A-3F show fixing an IM apparatus to a bone fragment according to one embodiment of the present disclosure. As shown in FIG. 3A, an IM nail 110 having at least three locking holes 112 is inserted into a medullary cavity 216 of the bone fragment 210 from the fractured end 212 of the bone fragment 210. The IM nail 110 is partially inserted into the medullary cavity 216 such that, as shown in FIG. 3B, at least one of the locking holes 112C is hidden by the bone fragment 210 and at least two of the locking holes 112A and 112B are exposed from the bone fragment 210. Thus, the two exposed locking holes 112A and 112B may be used for inserting two positioning members 132. As shown in FIG. 3C, the positional reference member 120 is mounted to the IM nail 110 by the two positioning members 132 inserted into the two exposed locking holes 112A and 112B, such that the longitudinal vernier scale 122 on the positional reference member 120 is parallel to the longitudinal axis of the IM nail 110. Since the locking holes 112 on the IM nail 110 are equally distantly defined thereon along the longitudinal axis, the longitudinal vernier scale 122 on the positional reference member 120 may be used as a reference scale to locate the hidden locking hole 112C.

Figure 3D:
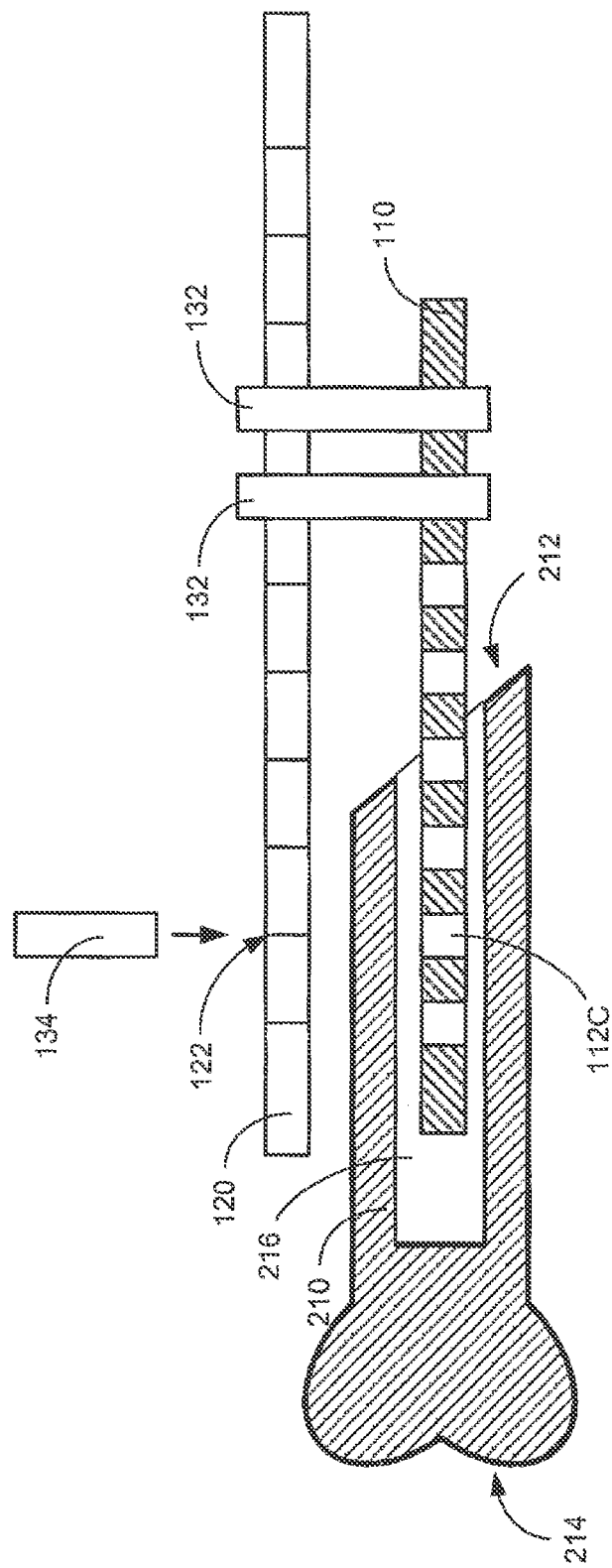
Figure 3E:
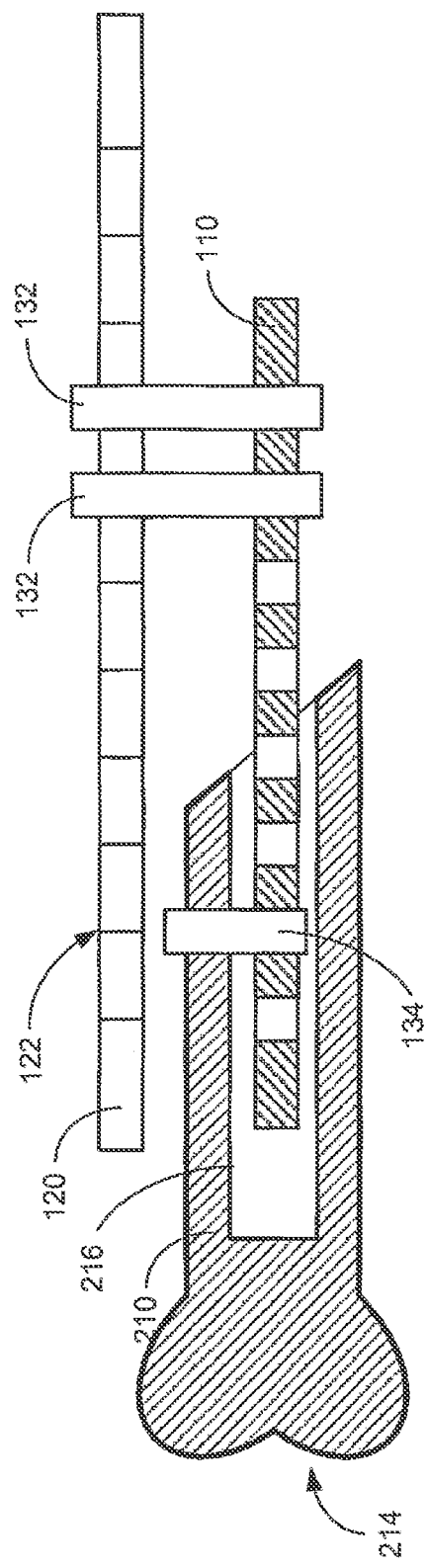
Figure 3F:
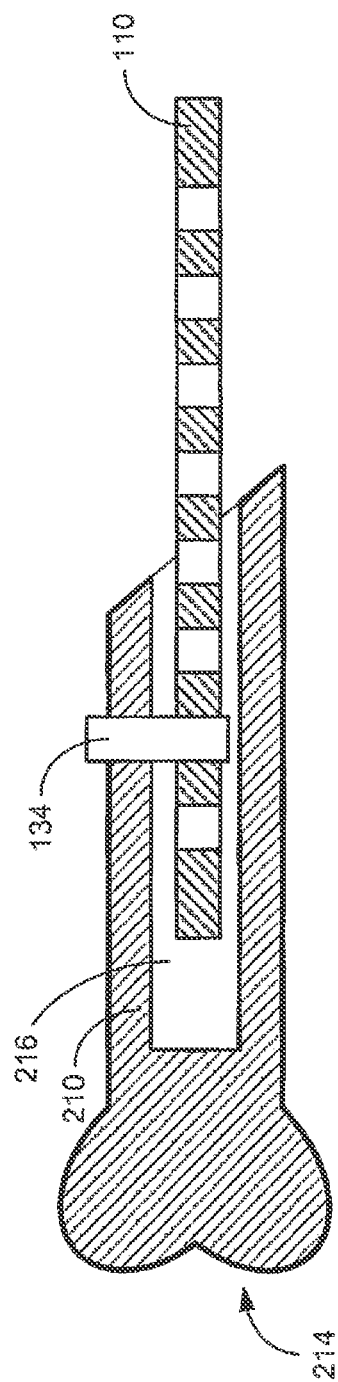

As shown in FIG. 3D, by using the longitudinal vernier scale 122 of the positional reference member 120, the position of the hidden locking hole 112C in the bone fragment 210 may be located. Thus, the doctor may drill a hole on the bone fragment 210 corresponding to the located hidden locking hole 112C such that the IM nail 110 is fixable to the bone fragment 210 by inserting the locking member 134 through the hole to the located hidden locking hole 112C. As shown in FIG. 3E, the IM nail 110 is fixed to the bone fragment 210 by inserting the locking member 134 to the located hidden locking hole 112C through the bone fragment 210. Then, the positional reference member 120 and the two positioning members 132 may be removed such that the IM nail 110 fixed to the bone fragment 210 is obtained, as shown in FIG. 3F.

Figure 4A:
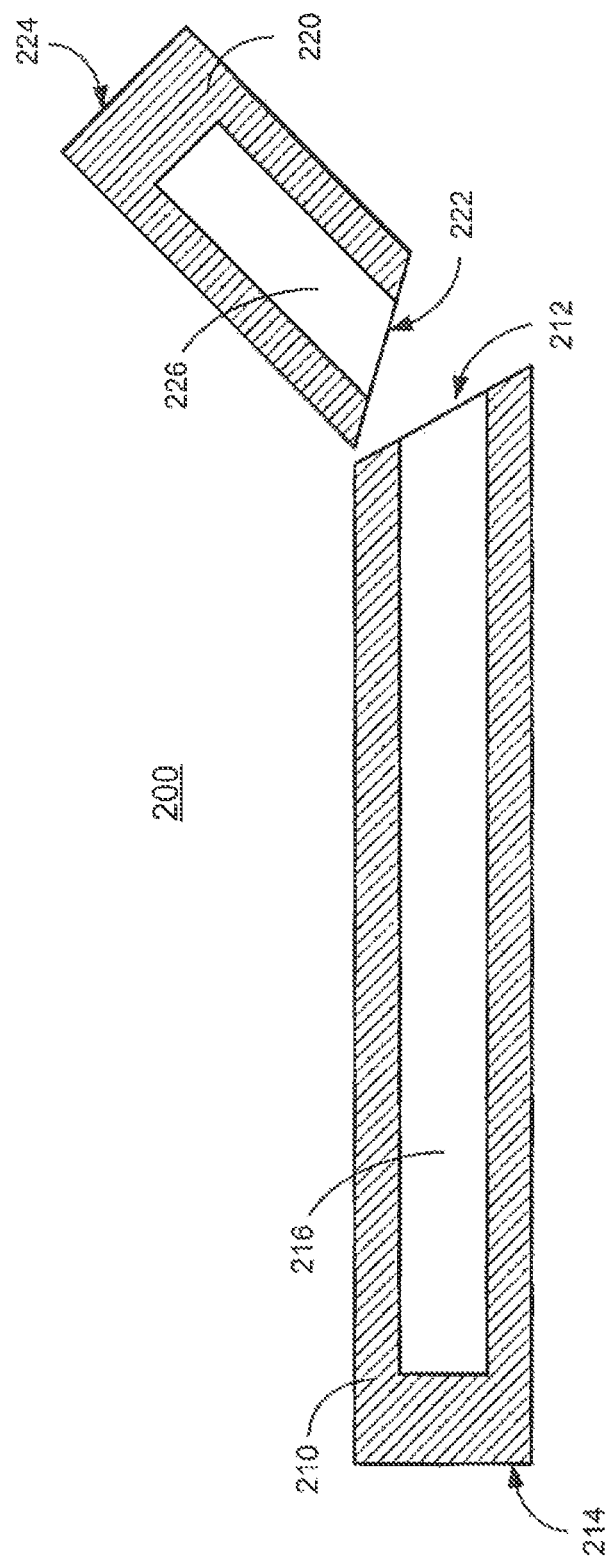
FIGS. 4A-4I show treating a fractured bone using an IM apparatus according to one embodiment of the present disclosure.

FIGS. 4A-4I show treating a fractured bone using an IM apparatus according to one embodiment of the present disclosure. As shown in FIG. 4A, the fractured bone 200 is fractured into two bone fragments, including a first bone fragment 210 and a second bone fragment 220. The first bone fragment 210 has a fractured end 212 and a joint end 214, and has a medullary cavity 216. Similarly, the second bone fragment 220 has a fractured end 222 and a joint end 224, and has a medullary cavity 226.

Figure 4B:
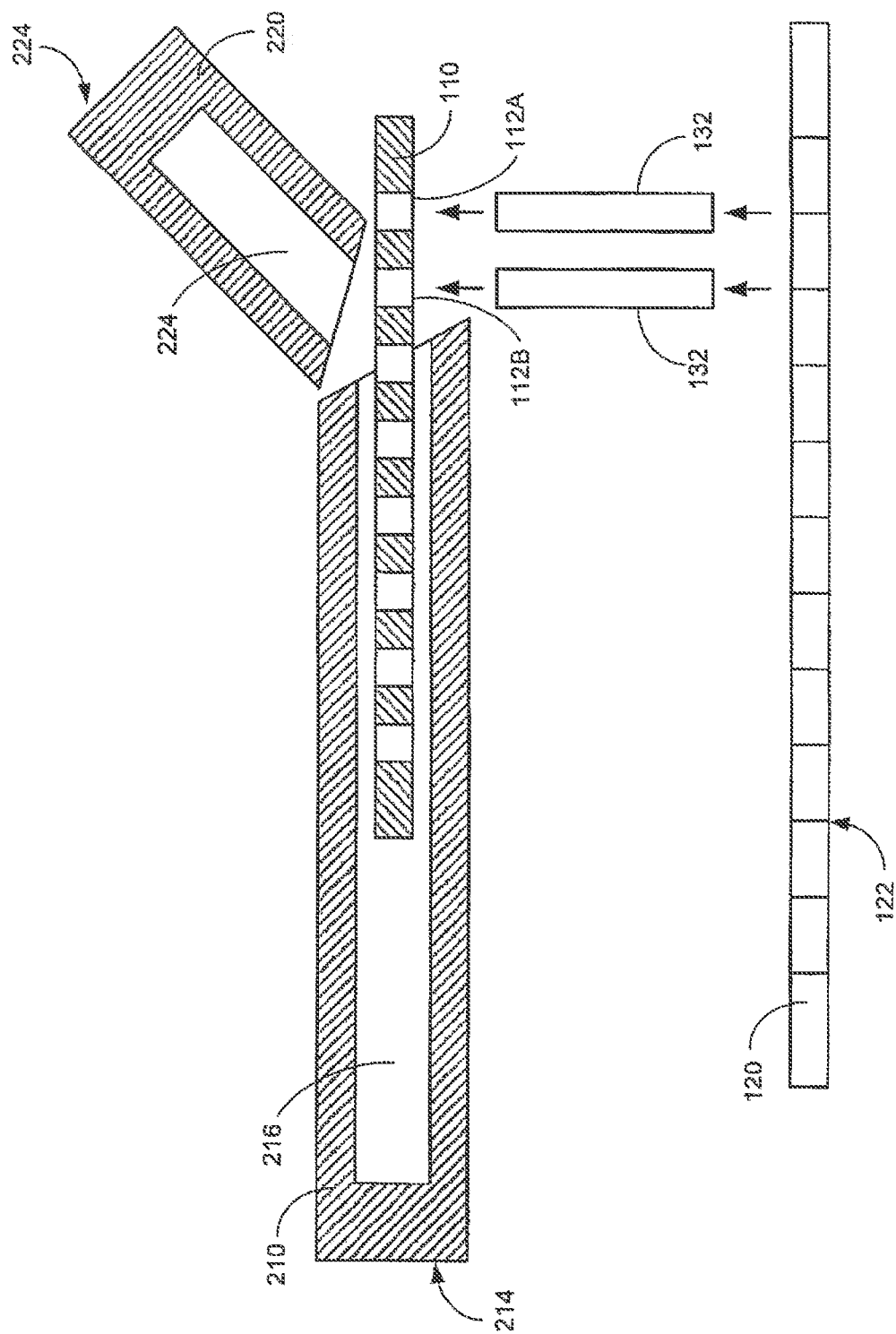

As shown in FIG. 4B, the IM nail 110 is inserted into the medullary cavity 216 of the first bone fragment 210 of the fractured bone 200 from the fracture end 212 of the first bone fragment 210. Thus, at least two of the locking holes 112 are hidden in the first bone fragment 210, and an exposed part of the IM nail 110 from the fracture end 212 of the first bone fragment 210 has at least two of the locking holes 112A and 112B. Thus, the positional reference member 120 may be mounted to the IM nail 110 by the two positioning members 132 inserted into the at least two exposed locking holes 112A and 112B.

Figure 4C:
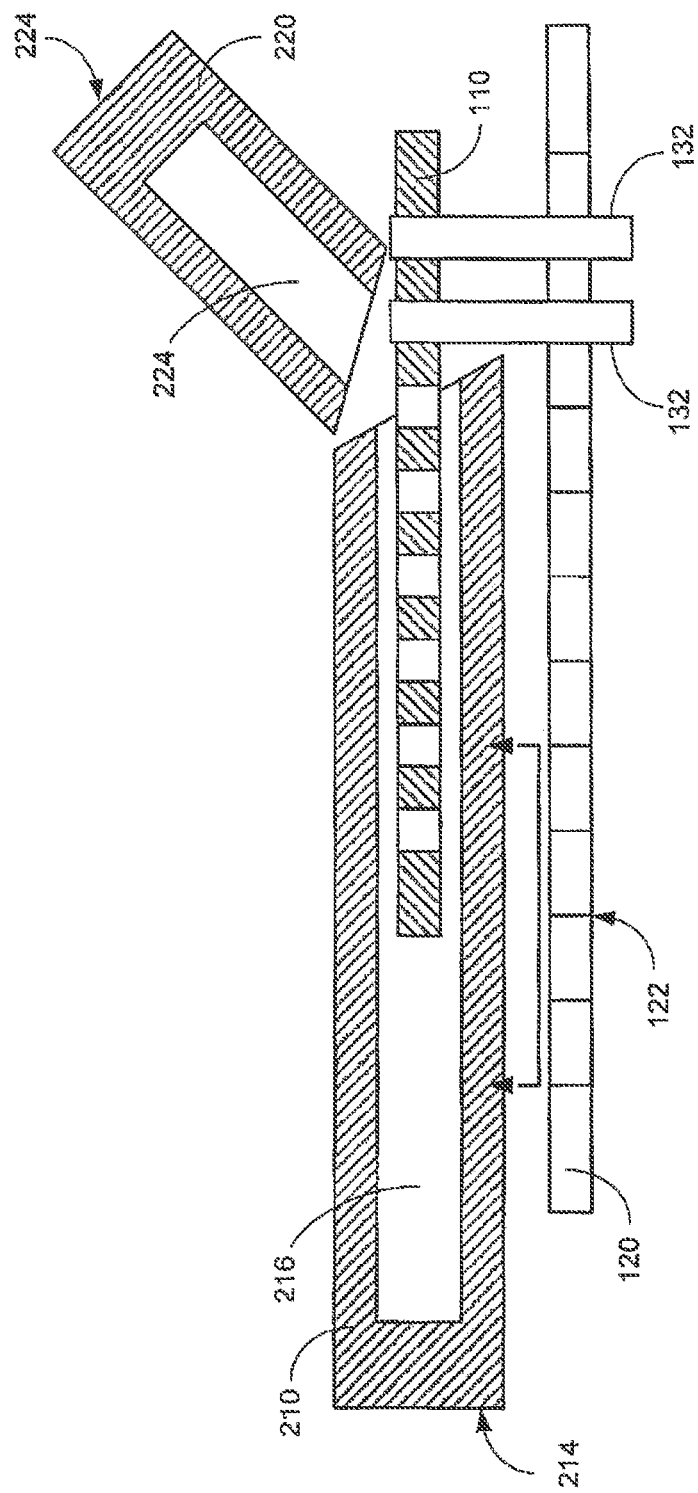
Figure 4D:
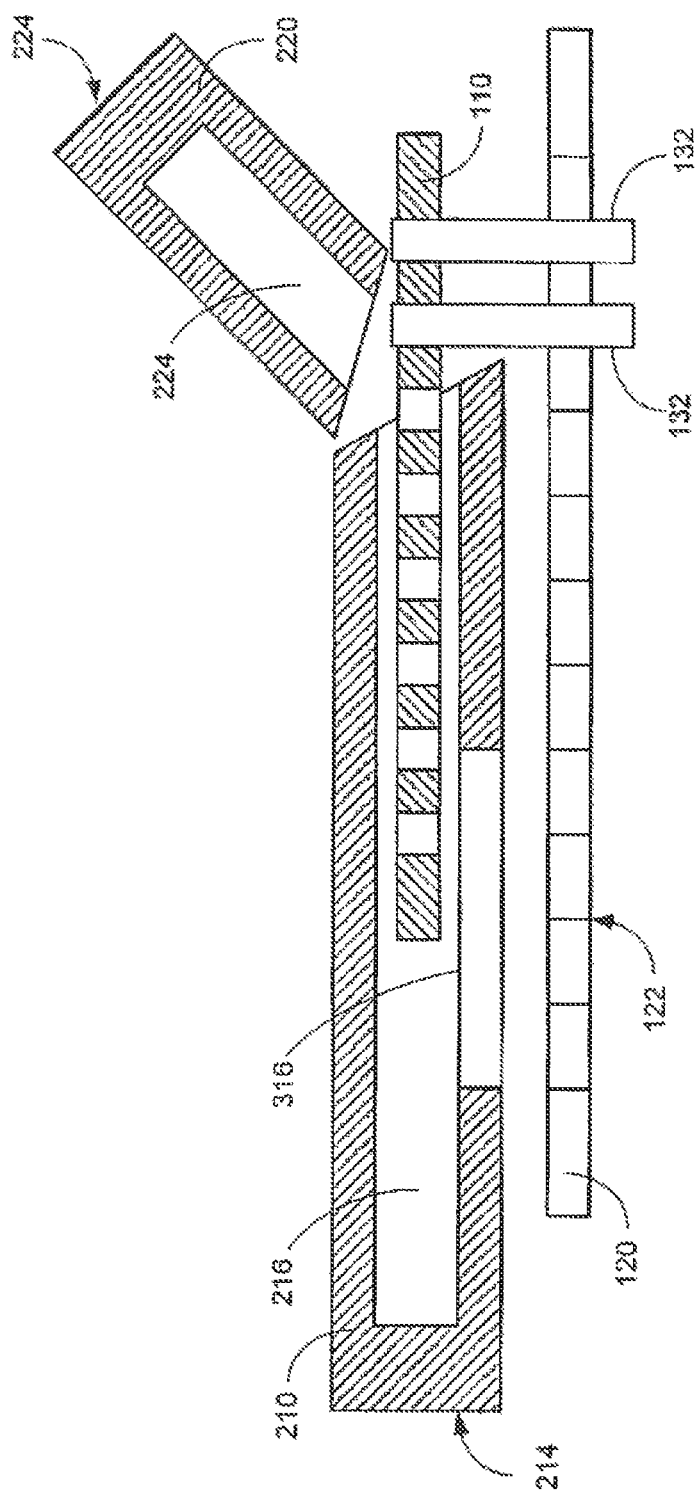

When the positional reference member 120 is mounted to the LM nail 110, as shown in FIG. 4C, the doctor may use the longitudinal vernier scale 122 on the positional reference member 120 as a reference for cutting a slot along the longitudinal axis on the first bone fragment 210. As shown in FIG. 4D, the slot 316 is formed to have a length such that at least two of the hidden locking holes 112 in the first bone fragment 210 may be exposed through the slot 316.

Figure 4E:
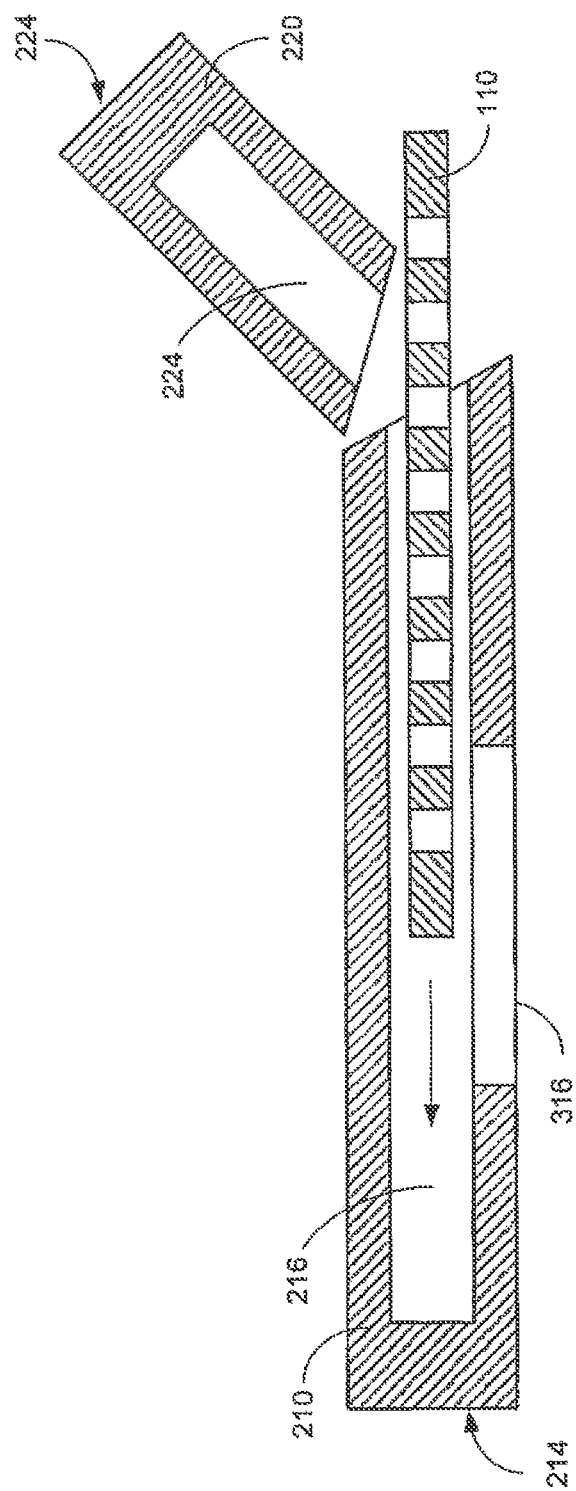
Figure 4F:
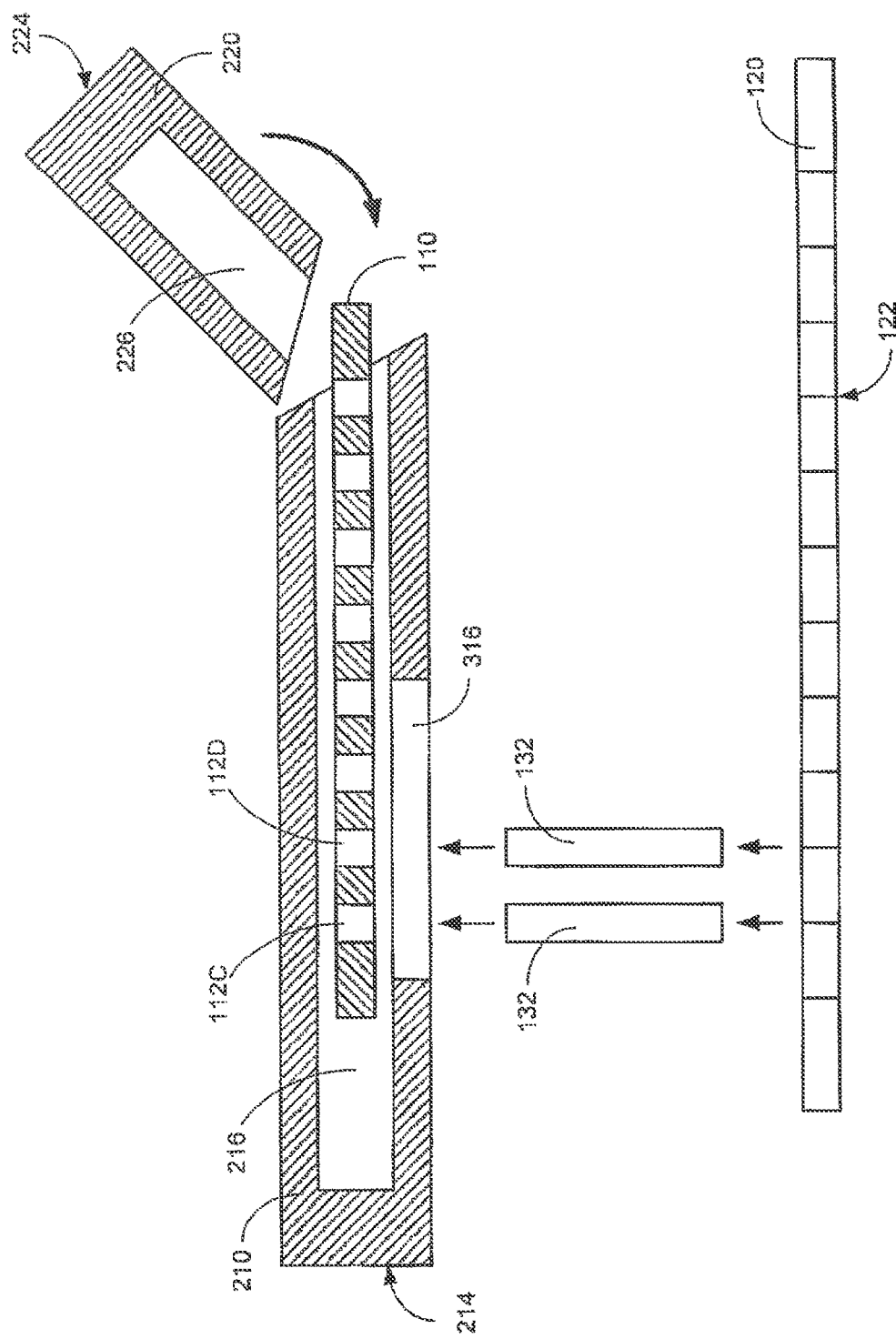

Then, as shown in FIG. 4E, the positional reference member 120 and the two positioning members 132 may be removed, and the IM nail 110 may be pushed further into the medullary cavity 216 of the first bone fragment 210 such that at least two of the hidden locking holes 112 are exposed from the slot 316. As shown in FIG. 4F, the IM nail 110 is pushed into the medullary cavity 216 of the first bone fragment 210 such that at least two of the hidden locking holes 112C and 112D are exposed from the slot 316. Further, in this position, the exposed part of the IM nail 110 from the fracture end 212 of the first bone fragment 210 is short enough for the second bone fragment 220 to be forced back to its original position without being interfered by the IM nail 110. Thus, by forcing back the second bone fragment 220 to its original position, the exposed part of the IM nail 110 is inserted into the medullary cavity 226 of the second bone fragment 220 from the fracture end 222 of the second bone fragment 220 such that the locking hole 112 on the exposed part of the IM nail 110 is now hidden in the second bone fragment 220. Meanwhile, the positional reference member 120 may be mounted again to the IM nail 110 by the two positioning members 132 inserted into the at least two exposed locking holes 112C and 112D from the slot 316.

Figure 4G:
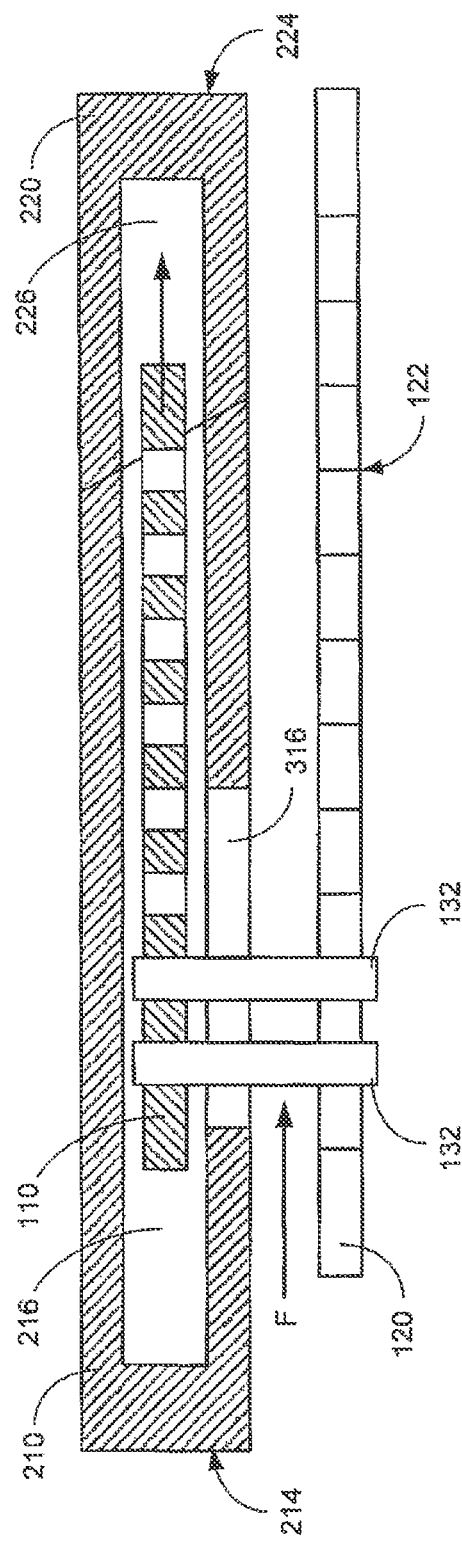

Then, as shown in FIG. 4G, the IM nail 110 is hidden in the medullary cavity 216 of the first bone fragment 210 and the medullary cavity 226 of the second bone fragment 220. However, the positional reference member 120 mounted on the IM nail 110 allows the doctor to push the positional reference member 120 with a force F, such that the IM nail 110 moves towards the second bone fragment 220. In this way, at least one of the locking holes 112 would be hidden in the second bone fragment 220.

Figure 4H:
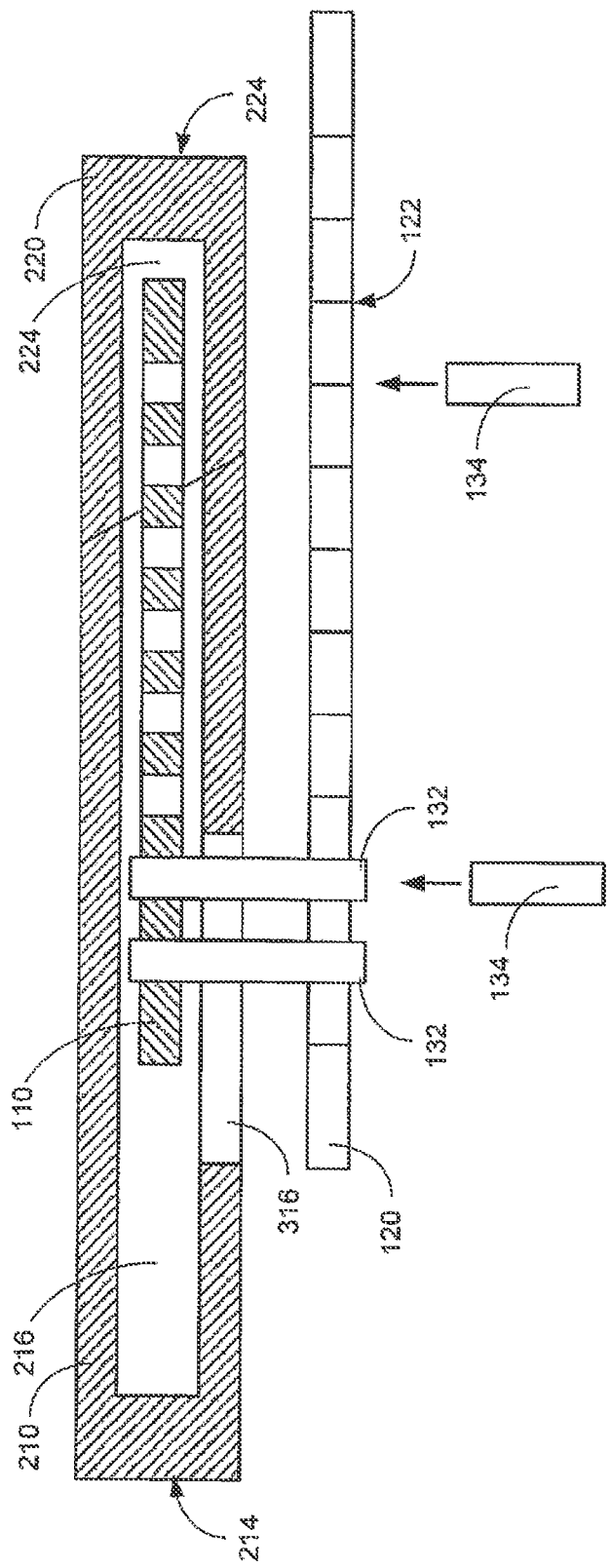
Figure 4I:
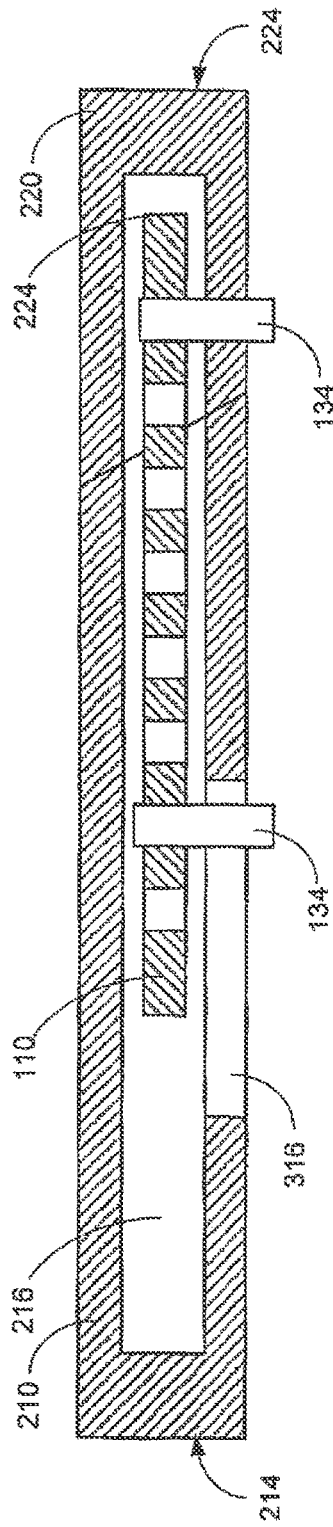

Thus, as shown in FIG. 4H, the doctor may use the longitudinal vernier scale 122 on the positional reference member 120 as a reference for locating the hidden locking hole 112 in the second bone fragment 220. Thus, the doctor may drill a hole on the second bone fragment 220 corresponding to the located hidden locking hole such that the IM nail 110 is fixable to the second bone fragment 220 by inserting the locking member 134 through the hole to the located hidden locking hole 112 in the second bone fragment 220. Similarly, the positional reference member 120 and the two positioning members 132 may be removed, and a locking member 134 may be inserted to the locking hole 112 exposed from the slot 316 to fix the IM nail 110 to the first bone fragment 210. Accordingly, as shown in FIG. 4I, the IM nail 110 is now fixed to the first bone fragment 210 and the second bone fragment 220 by the locking members 134.

It should be appreciated that in the method of treating the fractured bone using the IM apparatus as described in FIGS. 4A-4I, the length of the IM nail 110 can be shorter than the length of the medullary cavity 216 of the first bone fragment 210. Thus, as shown in FIG. 4G, when the IM nail 110 is substantially hidden in the medullary cavity 216 of the first bone fragment 210, the doctor may control the hidden IM nail 110 with the positional reference member 120 mounted to the IM nail 110 through the slot 316. Thus, there is no need to push the IM nail 110 to pass through the joint end 214 of the first bone fragment 210. Accordingly, the method of treating the fractured bone may not damage the joint connected to the fractured bone.

Figure 4J:
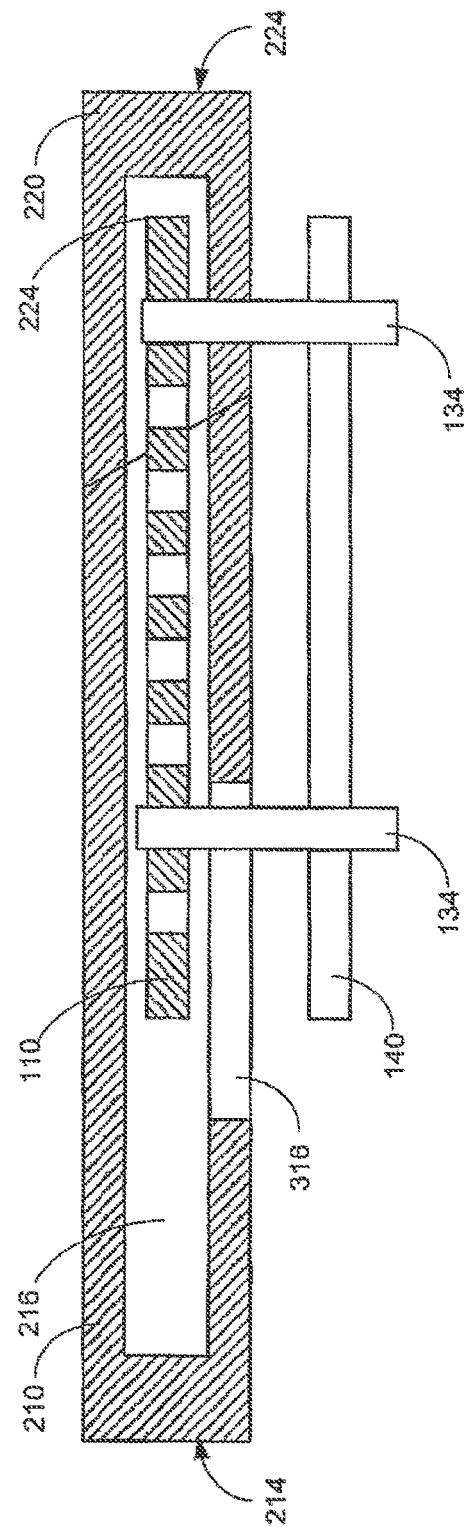
FIG. 4J shows treating a fractured bone using an IM apparatus according to another embodiment of the present disclosure.

In certain embodiment, the IM apparatus may further include an additional plate 140 for strengthening the fixing of the IM nail 110. For example, as shown in FIG. 4J, the plate 140 may be provided and positioned outside the first and second bone fragments 210 and 220 and detachably fixed to the bone fragments 210 and 220 and the IM nail 110 by the locking members 134. Thus, the plate 140 may reinforce the structure of the IM nail 110 to provide a strengthened fixing of the fractured bone.

It should be appreciated that the locking members 134 and the positioning members 132 may be screws, pins or other fixing or locking structure or device, and the size and length of the locking members 134 and the positioning members 132 may vary. In certain embodiments, the locking members 134 and the positioning members 132 may be the same locking structures or devices. Thus, although the positioning members 132 are shown in the figures as relatively long structures and the locking members 134 are shown in the figures as relatively short structures, the length of the locking members 134 may be the same as or longer than the length of the positioning members 132.

Figure 5A:
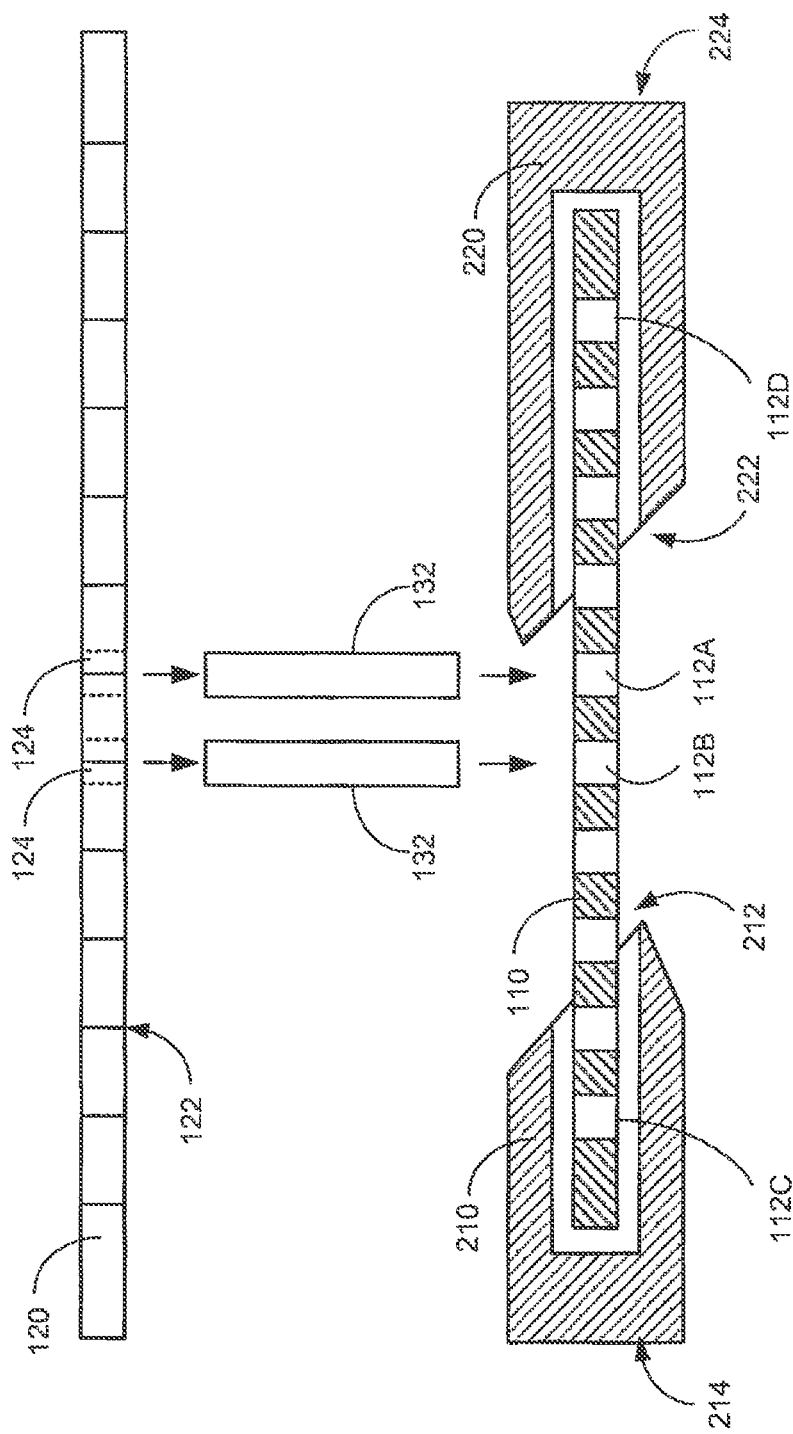
FIGS. 5A-5D show treating a comminuted fractured bone using an IM apparatus according to one embodiment of the present disclosure.

FIGS. 5A-5D show treating a comminuted fractured bone using an IM apparatus according to one embodiment of the present disclosure. As shown in FIG. 5A, when the comminuted fractured bone includes more than two pieces of bone fragments, the IM nail 110 may be inserted to the two bone fragments 210 and 220 at the two ends of the bone. Specifically, the IM nail 110 is inserted into the medullary cavity of the first bone fragment 210 from its fracture end 212 such that at least one of the locking holes 112C is hidden in the first bone fragment 210, and an exposed part of the IM nail 110 from the fracture end 212 of the first bone fragment 210 has at least three of the locking holes 112. Then, the exposed part of the IM nail 110 is inserted into the medullary cavity of the second bone fragment 220 from its fracture end 222 such that at least one of the exposed locking holes 112 is hidden in the second bone fragment 220, and at least two of the locking holes 112 remain exposed. In this way, the two exposed locking holes 112 may be used for inserting two positioning members 132. As shown in FIG. 5A, the positional reference member 120 is mounted to the IM nail 110 by the two positioning members 132 inserted into the two exposed locking holes 112, such that the longitudinal vernier scale 122 on the positional reference member 120 is parallel to the longitudinal axis of the IM nail 110. Since the locking holes 112 on the IM nail 110 are equally distantly defined thereon along the longitudinal axis, the longitudinal vernier scale 122 on the positional reference member 120 may be used as a reference scale to locate the hidden locking holes 112 in the first bone fragment 210 and the second bone fragment 220.

Figure 5B:
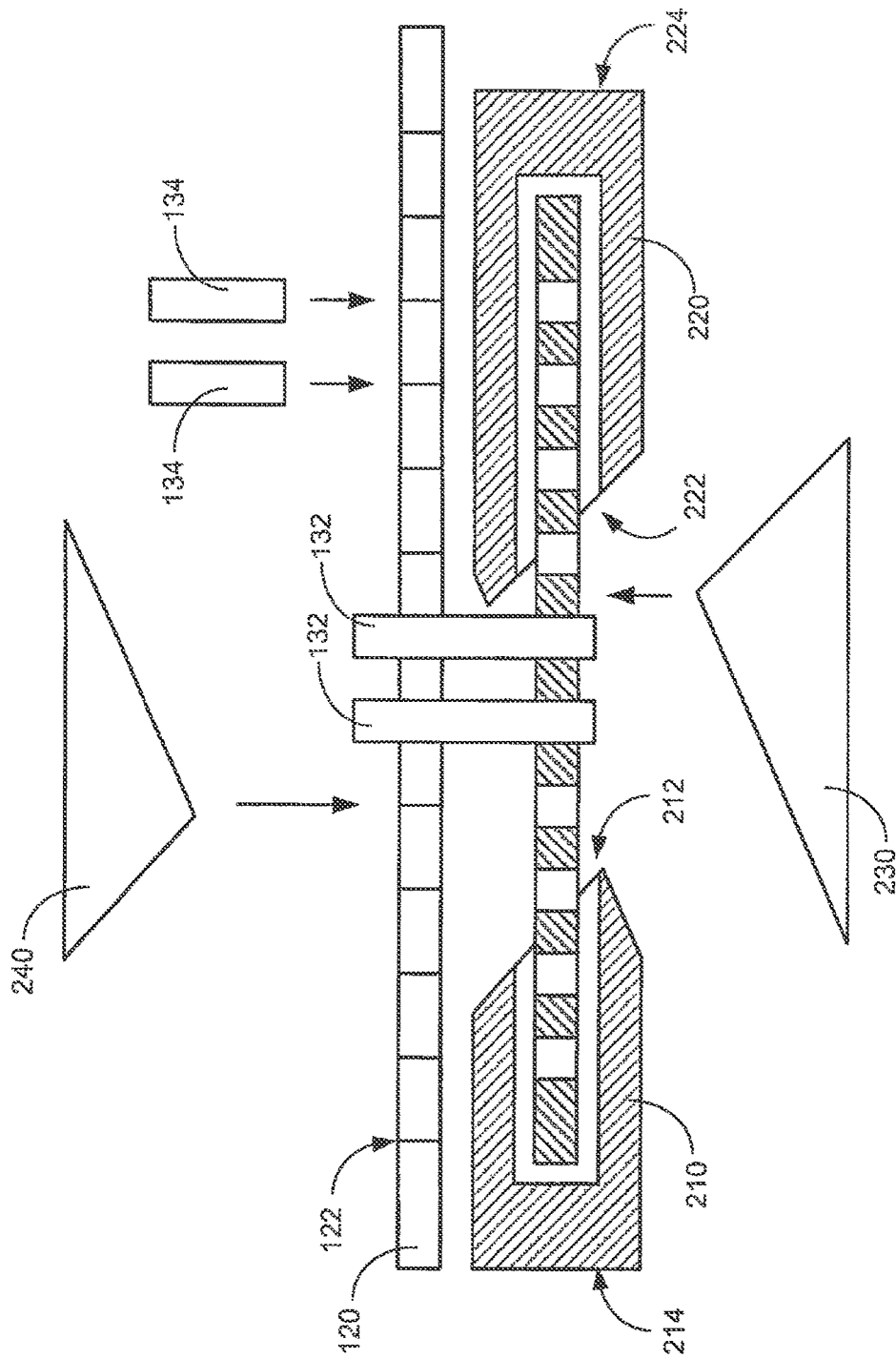

As shown in FIG. 5B, the IM nail 110 is fixed to the second bone fragment 220 by inserting two locking members 134 to the located hidden locking holes 112 through the second bone fragment 220. Meanwhile, the positional reference member 120 and the two positioning members 132 may be removed such that the third bone fragment 240 on the top side of the figure may be disposed on the IM nail 110. Similarly, the third bone fragment 230 on the bottom side of the figure may be disposed on the IM nail 110. Each of the third bone fragments 230 and 240 corresponds to at least one of the exposed locking holes 112 such that the third bone fragments 230 and 240 may be respectively fixed to the IM nail 110 by the locking member 134.

Figure 5C:
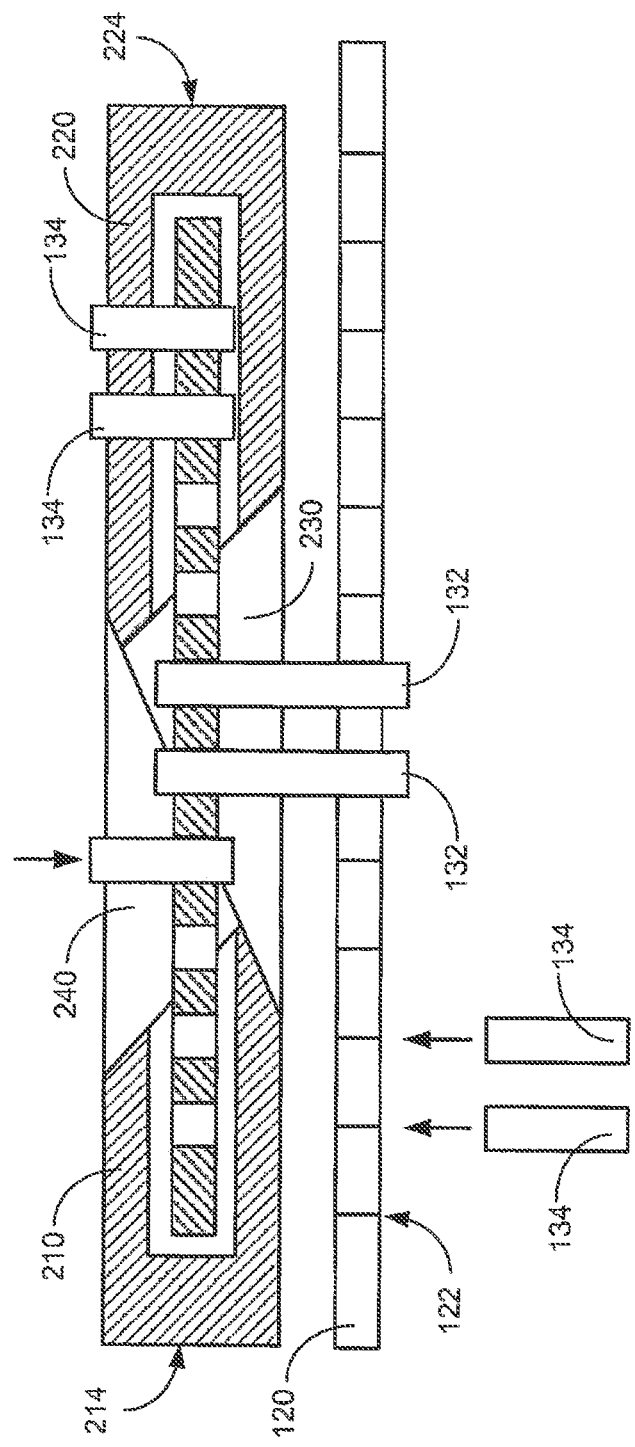
Figure 5D:
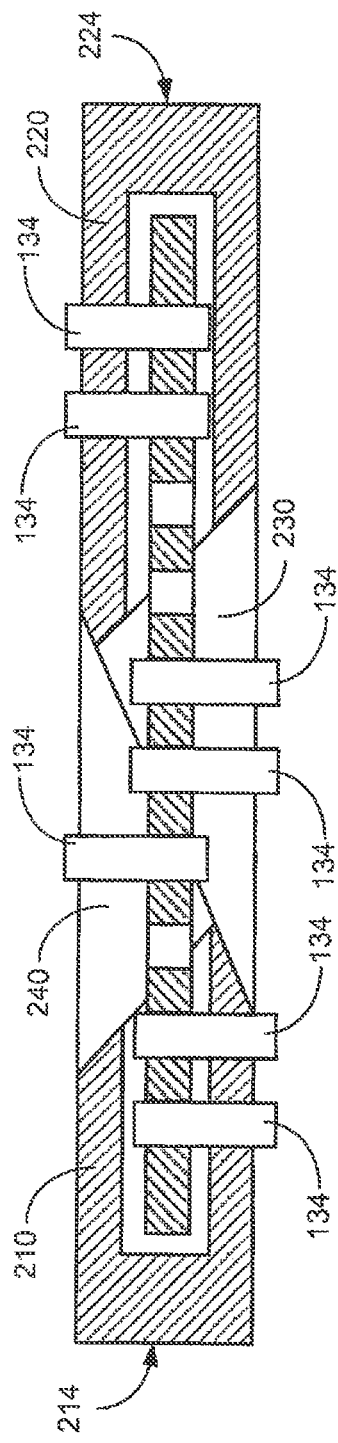

During the process of fixing the third bone fragments 230 and 240, it should be noted that the positional reference member 120 and the two positioning members 132 may be removed and re-mounted to the IM nail 110 for locating the hidden locking holes 112 in the bone fragments. For example, FIG. 5C shows that the positional reference member 120 is re-mounted on the bottom side of the figure such that the hidden locking holes 112 in the first bone fragment 210 may be located from the bottom side of the figure. Thus, as shown in FIG. 5D, all of the bone fragments 210, 220, 230 and 240 may be fixed to the IM nail 110 by the locking members 134 such that the relative positions of each bone fragment may be maintained.

Figure 5E:
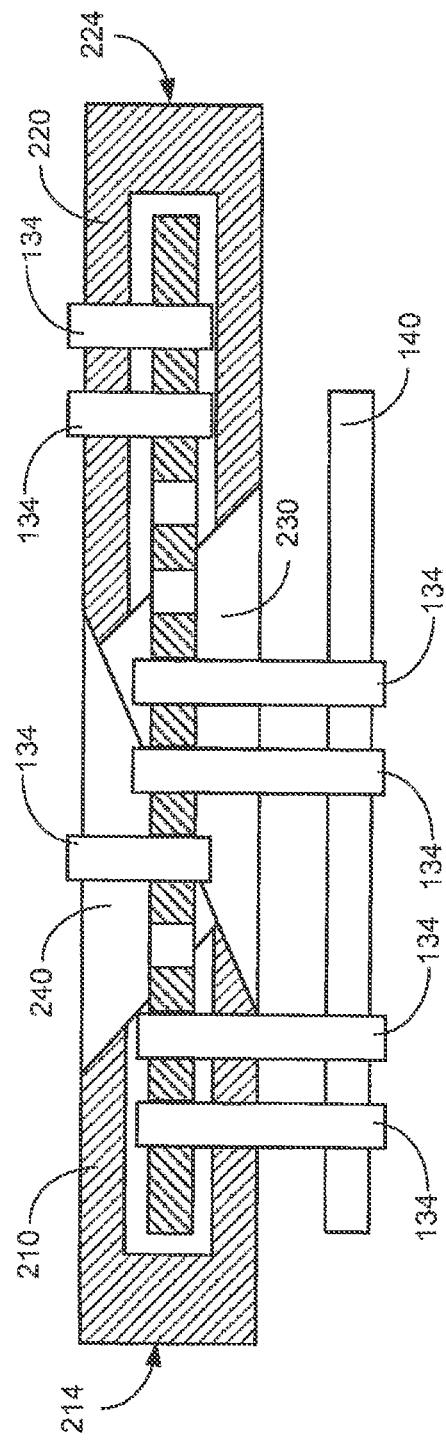
FIG. 5E shows treating a comminuted fractured bone using an IM apparatus according to another embodiment of the present disclosure.

In certain embodiment, the IM apparatus may further include an additional plate 140 for strengthening the fixing of the IM nail 110. For example, as shown in FIG. 5E, the plate 140 may be provided and positioned outside the first and second bone fragments 210 and 220 and detachably fixed to the bone fragments 210 and 220 and the IM nail 110 by the locking members 134. Thus, the plate 140 may reinforce the structure of the IM nail 110 to provide a strengthened fixing of the comminuted fractured bone.

It should be appreciated that the method as described in the present disclosure relates to treating a fractured bone of an animal. Specifically, the method can be used on any animal having a fractured bone. Examples of the animals being treated include human beings, dogs, cats and other mammals, or any other vertebrates with endoskeleton structures or internal bone structures.

In sum, the present disclosure relates to an IM apparatus for treating a fractured bone of an animal and applications of the same. By using the IM apparatus, the locking holes hidden in the bone fragments may be accurately located by the positional reference member, and the doctor may control the position of the IM nail hidden in the bone fragments by holding the positional reference member mounted to the IM nail.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed:

1. A method of treating a fractured bone of an animal using an intramedullary (IM) apparatus, the method comprising:

inserting an IM nail into a medullary cavity of a first bone fragment of the fractured bone from a fracture end of the first bone fragment, wherein the IM nail is elongated along a longitudinal axis and has a plurality of locking holes positioned along the longitudinal axis, such that the locking holes are hidden in the first bone fragment, and an exposed part of the IM nail from the fracture end of the first bone fragment has at least two of the locking holes;

cutting a slot along the longitudinal axis on the first bone fragment, such that at least two of the hidden locking holes in the first bone fragment are exposed through the slot;

mounting a positional reference member to the IM nail by two positioning members inserted into the at least two exposed locking holes through the slot, such that a longitudinal vernier scale on the positional reference member is parallel to the longitudinal axis of the IM nail;

inserting the exposed part of the IM nail into a medullary cavity of a second bone fragment of the fractured bone from a fracture end of the second bone fragment such that at least one of the locking holes on the exposed part of the IM nail is hidden in the second bone fragment; and locating the at least one hidden locking hole in the second bone fragment by the longitudinal vernier scale of the positional reference member; and fixing the IM nail to the second bone fragment by inserting a locking member to the located hidden locking hole through the second bone fragment.

2. The method as claimed in claim 1, further comprises:
    removing the positional reference member and positioning members, and fixing the 1M nail to the first bone fragment by positioning locking members to the at least two exposed locking holes through the slot.

3. The method as claimed in claim 1, further comprises:
    moving the IM nail in the first bone fragment towards the second bone fragment by pushing the positioning members along the slot towards the fracturing end of the first bone fragment.

4. The method as claimed in claim 1, further comprises:
    drilling a hole on the second bone fragment corresponding to the located hidden locking hole such that the 1M nail is fixable to the second bone fragment by inserting the locking member through the hole to the located hidden locking hole.

5. The method as claimed in claim 1, wherein the locking member and the positioning members are screws, and the locking holes are screw holes corresponding to the screws.

6. The method as claimed in claim 1, wherein the 1M nail is made of a metal or dissolvable artificial skeletal material.

* * * * *